(12) United States Patent
Melz et al.

(10) Patent No.: US 7,174,786 B2
(45) Date of Patent: Feb. 13, 2007

(54) QUALITY TESTING PROCESS

(75) Inventors: Matthias Melz, Berlin (DE); Jan Micko, Kosice (SK); Zhiguo Wang, Dachau (DE)

(73) Assignee: BSH Bosch und Siemens Hausgeraete GmbH, Munich (DE)

( * ) Notice: Subject to any disclaimer, the term of this patent is extended or adjusted under 35 U.S.C. 154(b) by 0 days.

(21) Appl. No.: 11/108,542

(22) Filed: Apr. 18, 2005

(65) Prior Publication Data

US 2005/0188767 A1    Sep. 1, 2005

Related U.S. Application Data

(63) Continuation of application No. PCT/EP03/11501, filed on Oct. 16, 2003.

(30) Foreign Application Priority Data

Oct. 17, 2002   (DE) ................. 102 48 511

(51) Int. Cl.
  *G01H 13/00* (2006.01)
  *G01M 7/02* (2006.01)
(52) U.S. Cl. ............. 73/579; 73/659; 73/660
(58) Field of Classification Search ........... 73/579, 73/659, 660, 664
  See application file for complete search history.

(56) References Cited

U.S. PATENT DOCUMENTS

| | | | |
|---|---|---|---|
| 4,988,979 A | 1/1991 | Sasaki et al. | |
| 5,062,296 A * | 11/1991 | Migliori | 73/579 |
| 5,528,924 A * | 6/1996 | Wajid et al. | 73/579 |
| 6,023,975 A * | 2/2000 | Willis | 73/579 |
| 6,098,022 A | 8/2000 | Sonnichsen et al. | |
| 6,289,735 B1 | 9/2001 | Dister et al. | |
| 2002/0046006 A1 | 4/2002 | Qian et al. | |
| 2005/0092087 A1* | 5/2005 | Kurt-Elli | 73/579 |

FOREIGN PATENT DOCUMENTS

SU    966518    10/1982

* cited by examiner

*Primary Examiner*—John E. Chapman
(74) *Attorney, Agent, or Firm*—Laurence A. Greenberg; Werner H. Stemer; Ralph E. Locher

(57) ABSTRACT

A process is performed for testing the quality of a unit such as an electromotor, which has at least one mobile part, which is mobile within a given frequency range with varying frequencies and is capable of exciting the unit to oscillate. In the method, a frequency of the mobile part at least within a first interval of the frequency range is varied with a first rate of change. The frequency of the mobile part within at least a second interval of the frequency range is varied with a second rate of change. The second rate of change is lower than the first rate of change. The oscillation amplitude of the unit is recorded and the unit is assessed as useful or unusable by evaluation of the recorded oscillation amplitude.

13 Claims, 2 Drawing Sheets

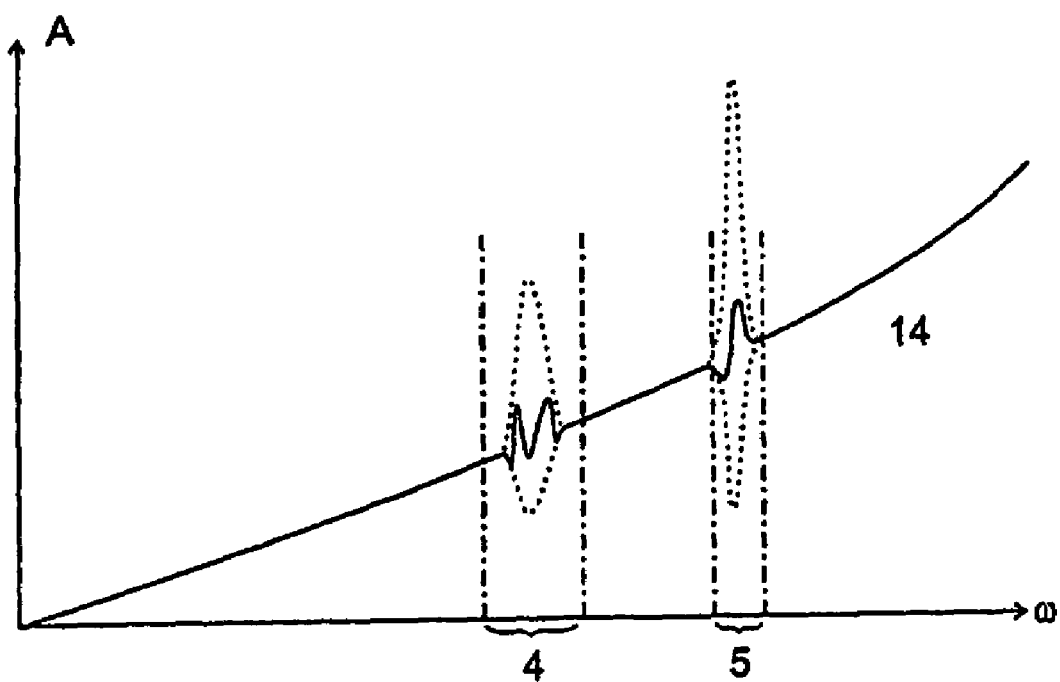

QUALITY TESTING PROCESS

CROSS-REFERENCE TO RELATED APPLICATION

This is a continuing application, under 35 U.S.C. § 120, of copending international application No. PCT/EP2003/011501, filed Oct. 16, 2003, which designated the United States; this application also claims the priority, under 35 U.S.C. § 119, of German patent application No. 102 48 511.9, filed Oct. 17, 2002; the prior applications are herewith incorporated by reference in their entirety.

BACKGROUND OF THE INVENTION

Field of the Invention

The present invention relates to a process for quality testing of units, which have periodically mobile parts with variable speeds. Movement of such parts, whether oscillation or vibration, can excite oscillations in another part of the unit. If the motion frequency of the exciting part matches a resonance frequency of the unit, the excited oscillation can reach considerable amplitudes, and this can lead to the radiation of clearly audible noises. These noises are unwanted for two reasons. For one, they are generally experienced by a person, within hearing range of the unit, as tiresome, plus excessive noise development of a unit, which clearly exceeds that of identical units from the same production batch, is often indicative of a fault, which does not necessarily introduce immediate unusability of the unit, which, however, boasts a shorter service life at least in a unit making stronger noises than in a unit not doing so. Prior to installation of such a unit in a complex device it is therefore appropriate to carry out quality testing of the unit by its noise development at different operating speeds, to be able to sort out units of doubtful quality, if required.

In order to assess the quality of a unit by way of its noise development, each speed, which can accept its mobile parts, would have to be set theoretically and the resulting oscillation amplitudes recorded for the relevant speed. The simplest possibility of achieving this is to continuously vary the speed of a mobile part within the given range of possible speeds over time and to record the various resulting oscillation amplitudes over time.

But this gives rise to the problem that resonances of the unit, if they were to occur, can have strongly different damping and correspondingly different spectral widths. A strongly damped resonance in general has a large spectral width, so that, if the speed of the mobile part exciting the resonance is continuously varied, the time span, in which its speed is suited to exciting the resonance, is long enough for the resonance to also be observed. The less the damping, the less the spectral width of a resonance, and the shorter in a given rate of change of the frequency of the mobile part is the time span, in which the resonance can be excited.

If the frequency of the mobile part does not exactly match the resonance frequency, this leads to oscillations between the resonance and the periodic movement of the mobile part, that is, the resonance is alternately excited and damped by the movement of the mobile part. The amplitude, by which a resonance is actually observed, when it is excited by a periodic movement with uniformly increasing (or decreasing) frequency, therefore depends decisively on the relative phase position between exciting movement and resonance when both its frequencies match. This phase position is a random variable, however. Therefore it can happen in particular that the strength of weakly damped resonances is not recorded correctly, because the time span, in which the frequency of the movement of the exciting body intersects with the spectrum of the resonance, is too short to excite the resonance effectively, and/or because the movement of the body and the resonance oscillation are in an unfavorable phase position to one another when traveling through the resonance range, and this prevents effective exciting of the resonance oscillation.

The reliability, with which the strength of a resonance can be recorded, is also the greater the more slowly the movement frequency of a mobile part is varied, which could excite the resonance. But the more slowly the frequency is varied, the longer a testing procedure lasts, and the smaller the number of units which can be examined with a single testing device in a given time span.

So as to reduce the costs of quality testing an effort must be made to keep the time span required for quality testing as short as possible.

SUMMARY OF THE INVENTION

It is accordingly an object of the invention to provide a quality testing process which overcomes the above-mentioned disadvantages of the prior art methods of this general type, which enables quality testing in a short time, and which nevertheless allows accurate recording and assessing of resonances also of less spectral width.

With the foregoing and other objects in view there is provided, in accordance with the invention, A process for testing a quality of an unit having at least one mobile part being mobile within a given frequency range with different frequencies and capable of exciting the unit to oscillate. The method includes the steps of varying a frequency of the mobile part at least within a first interval of the given frequency range with a first rate of change and varying the frequency of the mobile part within at least a second interval of the given frequency range with a second rate of change. The second rate of change is lower than the first rate of change. The oscillation amplitude of the unit is recorded and the recorded oscillation amplitude is analyzed for assessing the unit as useable or unusable.

The task is solved according to the present invention in that the frequency of the mobile part is varied during the process with two different rates of change, a first, suited to "superficial" examination and must not enable quantitative evaluation of the strength of a resonance, and a second rate of change, which is lower than the first and thus enables a detailed examination of particularly interesting spectral ranges. The usefulness of a unit is evaluated by assessment of the oscillation amplitude recorded at least with the second rate of change.

In a first embodiment of the process the frequency interval to be examined is established in detail with the second rate of change by the oscillation amplitude previously recorded with the first rate of change. This preferably happens in that the entire frequency range to be examined is first fully traversed with the first rate of change, whereby present resonances emerge in general already in thus recorded oscillation amplitude, even when evaluation of the strength of the resonances is still not possible. The frequency intervals to be examined more precisely in this way and detected in a short time are then examined with the second, lower rate of change, which allows secure evaluation of the strength of the resonance.

According to a second embodiment of the invention it is sufficient for the frequency range to be examined to be traversed once continuously, whereby the rate of change in each case within a previously established interval to be examined precisely is kept to the second value and outside such an interval on the first value.

The ranges to be examined with the second rate of change ranges are established in this case preferably, where measurement of the present resonance frequencies is made in advance on a unit to be examined that is structurally identical to the unit. Because the resonance frequencies found in such a preliminary measuring for a plurality of testing procedures are useful in each case in structurally identical units, the preliminary measuring can be performed with a high time expenditure and high precision; the following measurements for quality assessment of the individual sets of components accordingly require only a short time.

Other features which are considered as characteristic for the invention are set forth in the appended claims.

Although the invention is illustrated and described herein as embodied in a quality testing process, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 4 is a graph showing an idealized curve of the oscillation amplitude as a function of the speed, which can be obtained in a first step of a process according to a second embodiment of the invention.

DESCRIPTION OF THE PREFERRED EMBODIMENTS

Figure 1:
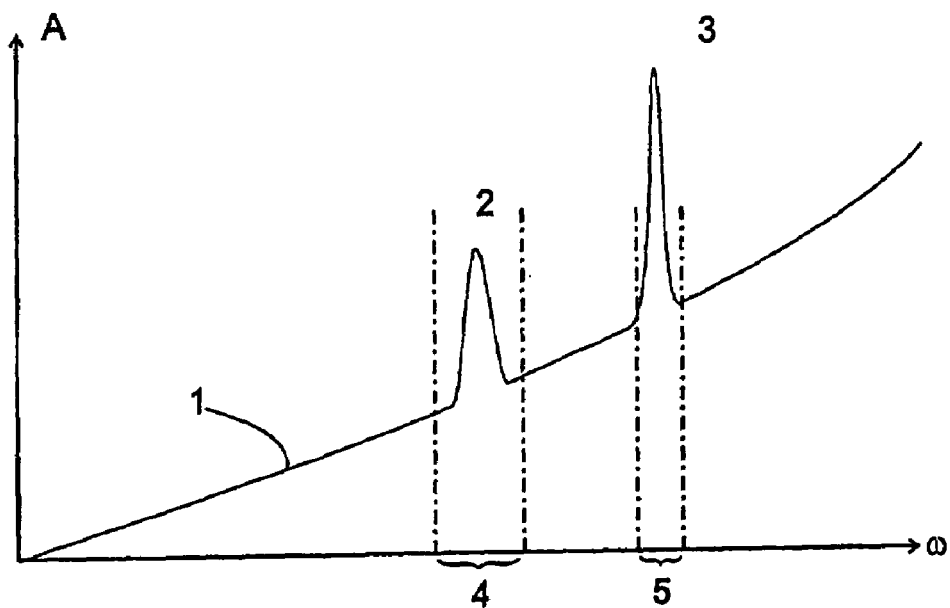
FIG. 1 is a graph showing an oscillation amplitude of a housing of an electromotor as a function of its speed according to the invention.

Referring now to the figures of the drawing in detail and first, particularly, to FIG. 1 thereof, there is shown a graph showing an oscillation amplitude A of a housing of an electromotor, applied in arbitrary units to the ordinate, as a function of the speed $\omega$ of its rotor, applied to the abscissa. The curve 1 shown in FIG. 1 is idealized insofar as each of its points correspond to respective measuring points, which would be obtained for the individual speeds $\omega$ for arbitrarily long measurement periods. In practice such a curve can only be made approximately, since no such long measuring times are available.

The curve 1, superimposed on a substrate growing with increasing speed $\omega$, shows two local extremes 2, 3, which correspond in each case to resonance frequencies of the examined motor. If several motors of the same series are examined, it is generally established that the speeds corresponding to the individual resonances differ only insignificantly from one motor to the next. The maximal oscillation amplitudes in the resonances, that is, the values of the amplitude at the extremes 2, 3 can vary sharply from motor to motor however.

Based on this knowledge in a first embodiment of the inventive process measuring of the resonance frequencies of motors of given construction is carried out on a sample copy or a limited number of sample copies. The number of examined sample copies is in general substantially smaller than the number of motors, on which quality testing is subsequently carried out, and the time expenditure for measuring the sample copies is therefore only minimally crucial in relation to time expenditure for the quality testing of the motors. The sample copies can thus be measured, where their speed is increased very slowly over time and meanwhile the amplitude of the housing oscillation is recorded and plotted as a function of the speed. With such measuring traversing of the speed range of such a motor from zero to a few thousand revolutions per minute can require a time span of several minutes.

The speed intervals, designated in FIG. 1 by 4, 5, in which the resonances of the housing lie, are determined from the resulting measured curves.

Figure 2:
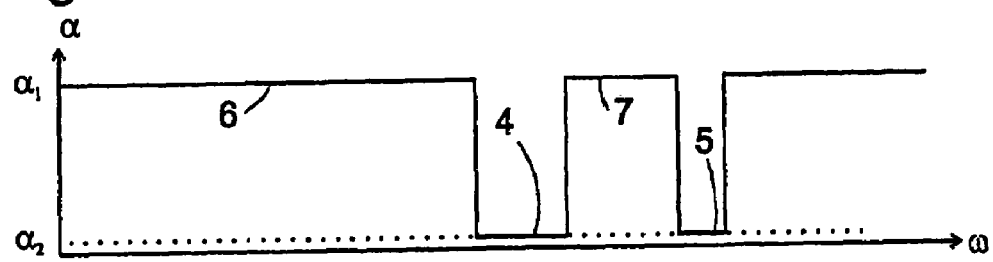
FIG. 2 is a graph showing the angular acceleration of a rotor during measuring as a function of the speed.

With subsequent quality testing of an individual motor its rotational speed varied from zero to the upper limit of its permissible speed range. The applied rate of change of speed or the angular acceleration $\alpha$ is shown in FIG. 2 as a function of the speed $\omega$. A first speed interval or range 6, in which the previously examined sample copies have exhibited no resonance, is traversed with a high angular acceleration $\alpha_1$. The angular acceleration is selected such that, as will become clearer still later, it allows the presence of a resonance to be recognized, though does not allow secure assessment of its strength. The angle acceleration $\alpha_1$ can be e.g. in a range of 5–20 rev/s$^2$, so that a speed range of 0–200 rev/s in a time span of 10–40 s can be traversed.

Figure 3:
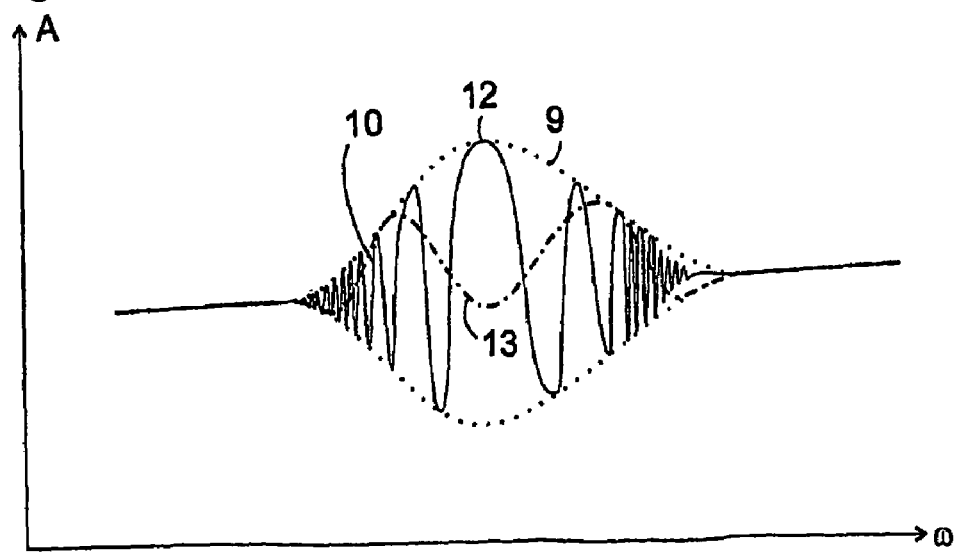
FIG. 3 is an idealized illustration of actually measured oscillation amplitude as a function of the speed in the vicinity of a resonance.

The speed interval 4 following the first interval 6 is traversed with angle acceleration $\alpha_2$, which is at a maximum $\frac{1}{10}$ to $\frac{1}{4}$ of $\alpha_1$. The angle acceleration $\alpha_2$ is selected such that during a time span, in which the angle velocity $\omega$ of the motor is in the region of a resonance, several beat periods can occur between the revolution of the rotor and the resonance. FIG. 3 shows, on a speed scale spread compared to FIG. 1, a typical trajectory of the oscillation amplitude, which could be recorded when traversing the interval 4 with the low angle acceleration $\alpha_2$. The trajectory of the resonance from FIG. 1 is illustrated in FIG. 3 as a dotted line 9. When the speed of the motor enters the edge region of the resonance on its way from low speeds, an oscillation occurs between the motor revolution and the housing resonance. Its frequency is high in the edge region of the resonance, obvious in FIG. 3 as rapid oscillating of the measured curve 10. The closer the speed comes to the exact resonance speed, the lower the frequency of the oscillation becomes, and the broader the individual periods of the measured curve 10 become. If the speed of the motor has exceeded that of the resonance speed, the oscillating frequency increases to the edge of the resonance. Because the angle acceleration $\alpha$ is low, while the angle velocity $\omega$ passes through the resonance, a large number of beat periods is plotted, also including those which are so near the exact resonance speed that their maximums such as point 12 permit a good conclusion to the actual maximum of the line 9 and thus of the strength of the resonance. Therefore reproducible measuring of the oscillation amplitude is obtained, which adjusts whenever the motor runs continuously with the resonance frequency. Reliable evaluation of the quality of the motor is possible by this amplitude.

If the angle acceleration α of the motor were clearly greater when passing through the interval 4, the number of the beat periods observed when passing through the resonance would reduce, and the resulting measured curve could have e.g. the form of the dotted curve 13 from FIG. 3. As is evident, its extremes remain clearly under the maximal amplitude of the resonance. However great the maximal amplitude measured during rapid passage in the individual case is, depends on the relative phase position between motor revolution and resonance oscillation. The relative phase position is a random variable however, making the amplitude measurements non-reproducible at high angle acceleration.

If the rotational frequency of the motor has left the interval 4, in a subsequent interval or range 7, in which no resonance is to be expected by the measured results obtained on the sample copies, the angle acceleration is reset to the high value $\alpha_1$. In the interval 5, in which a resonance of the housing is again to be expected, the angle acceleration is reset to the low second value $\alpha_2$ in order to precisely measure the corresponding resonance. This exchange is repeated as often as resonance frequency intervals were found in the measurements on the sample copies.

The width of a resonance speed interval 4 or 5 is typically about 100 rev/min. In the inventive process such an interval is preferably completed in 5–7 seconds, corresponding in a measuring duration per resonance of about 20 μs to angle acceleration of about 2–4 rev/s².

Complete measuring of the oscillation behavior of a motor can thus be completed within 15–20 seconds.

A second embodiment of the process is illustrated by FIG. 4. In this embodiment the entire speed interval of the motor is first traversed with the angular acceleration $\alpha_1$ and the resulting oscillation amplitudes A are plotted. FIG. 4 shows as an interrupted line 14 a typical trajectory of the resulting measured curve and in comparison to this the curve 1 from FIG. 1, which reflects the true oscillation amplitude in the stationary regime. The oscillation amplitudes occurring with passing through the resonances with the angle acceleration $\alpha_1$ allow no reliable estimation of the strength of a resonance. That a resonance is present can however be determined from observing the oscillations typical therefore in the intervals 4, 5 of the curve 14. These oscillations are easy to record metrologically by deriving the measured curve 14 according to the speed ω, forming the amount of derivation and seeking those frequency ranges, in which the derivation amount exceeds a limit value.

If ranges of the measured curve 14 have been determined in this way as the illustrated intervals 4, 5, at which resonances could occur, these intervals are then traversed with the second angle acceleration $\alpha_2$. In this way a measuring signal is received here too, as shown by the curve 10 in FIG. 3, and accurate evaluation of the strength of the resonance is possible by examination of the extremes of the curve 10.

The time expenditure for a single quality testing is slightly greater with the process according to the second embodiment than with the first method, since in the second embodiment the speed intervals 4, 5, in which the fast first measurement has resulted in suspicion of resonance, a second time would have to be measured, whereas in the first embodiment the entire interesting frequency range is traversed only once, though with alternating acceleration values $\alpha_1$, $\alpha_2$. But the enlarged measuring time advantageously opposes the fact that no previous knowledge on the possible position of resonances is required, and that also preliminary measurements on sample copies are superfluous.

We claim:

1. A process for testing a quality of an unit having at least one mobile part being mobile within a given frequency range with different frequencies and capable of exciting the unit to oscillate, which comprises the steps of:
    a) varying a frequency of the mobile part at least within a first interval of the given frequency range with a first rate of change for exciting the unit to oscillate;
    b) varying the frequency of the mobile part within at least a second interval of the given frequency range with a second rate of change, the second rate of change being lower than the first rate of change for exciting the unit to oscillate;
    c) recording an oscillation amplitude of the unit resulting in a recorded oscillation amplitude; and
    d) analyzing the recorded oscillation amplitude for assessing the unit as useable or unusable.

2. The process according to claim 1, which further comprises evaluating the recorded oscillation amplitude obtained during step a) for ascertaining the second interval of the given frequency range to be tested during step b).

3. The process according to claim 1, which further comprises:
    carrying out step a) completely for the given frequency range fully with the first rate of change; and
    carrying out step b) for the second interval of the given frequency range with the second rate of change.

4. The process according to claim 1, which further comprises carrying out the given frequency range continuously, whereby a rate of change within each second interval is maintained at the second rate of change and outside each of the second intervals the rate of change is carried out with the first rate of change.

5. The process according to claim 1, which further comprises establishing the second interval prior to carrying out steps a) and b).

6. The process according to claim 5, which further comprises establishing at least the second interval by recording the oscillation amplitude of a comparable unit with the unit to be tested in dependence on the frequency.

7. The process according to claim 1, which further comprises using an electric machine as the unit.

8. The process according to claim 1, which further comprises using an electromotor as the unit.

9. The process according to claim 1, which further comprises setting the second rate of change to be less than a quarter of the first rate of change.

10. The process according to claim 1, which further comprises setting the second rate of change to be less than a tenth of the first rate of change.

11. A process for testing a quality of an unit having at least one mobile part being mobile within a given frequency range with different frequencies and capable of exciting the unit to oscillate, which comprises the steps of:
    a) varying a frequency of the mobile part at least within a first interval of the given frequency range with a first rate of change;
    b) varying the frequency of the mobile part within at least a second interval of the given frequency range with a second rate of change, the second interval being established prior to carrying out steps a) and b), and the second rate of change being lower than the first rate of change;
    c) recording an oscillation amplitude of the unit resulting in a recorded oscillation amplitude; and
    d) analyzing the recorded oscillation amplitude for assessing the unit as useable or unusable.

12. The process according to claim 11, which further comprises establishing at least the second interval by recording the oscillation amplitude of a comparable unit with the unit to be tested in dependence on the frequency.

13. A process for testing a quality of a motor having at least one rotor being mobile within a given frequency range with different frequencies and being capable of exciting the motor to oscillate, the process comprising the following steps:
   a) varying a frequency of the rotor at least within a first interval of the given frequency range with a first rate of change for exciting the motor to oscillate;
   b) varying the frequency of the rotor within at least a second interval of the given frequency range with a second rate of change, the second rate of change being lower than the first rate of change for exciting the motor to oscillate;
   c) recording an oscillation amplitude of the motor resulting in a recorded oscillation amplitude; and
   d) analyzing the recorded oscillation amplitude for assessing the motor as useable or unusable.

* * * * *